(12) United States Patent
Maier

(10) Patent No.: US 8,271,070 B2
(45) Date of Patent: Sep. 18, 2012

(54) METHOD FOR MONITORING MYOCARDIAL WALL THICKNESS

(75) Inventor: Corinna Maier, Princeton, NJ (US)

(73) Assignee: Siemens Aktiengesellschaft, München (DE)

(*) Notice: Subject to any disclaimer, the term of this patent is extended or adjusted under 35 U.S.C. 154(b) by 946 days.

(21) Appl. No.: 12/041,151

(22) Filed: Mar. 3, 2008

(65) Prior Publication Data

US 2009/0093699 A1    Apr. 9, 2009

Related U.S. Application Data

(60) Provisional application No. 60/977,392, filed on Oct. 4, 2007.

(51) Int. Cl.
*A61B 6/00* (2006.01)

(52) U.S. Cl. .................. 600/425; 382/173; 600/523

(58) Field of Classification Search ............. 382/128, 382/130, 173, 107; 701/213; 600/374, 443, 600/447, 450, 459, 407, 410, 425, 438, 508, 600/523; 324/306, 309
See application file for complete search history.

(56) References Cited

U.S. PATENT DOCUMENTS

| | | | | |
|---|---|---|---|---|
| 4,723,536 A * | 2/1988 | Rauscher et al. | .............. | 600/14 |
| 4,889,526 A * | 12/1989 | Rauscher et al. | .............. | 600/14 |
| 5,544,656 A * | 8/1996 | Pitsillides et al. | ............ | 600/450 |
| 5,560,367 A * | 10/1996 | Haardt et al. | ................ | 600/515 |
| 5,768,413 A * | 6/1998 | Levin et al. | ................... | 382/173 |
| 6,031,374 A * | 2/2000 | Epstein et al. | ............... | 324/306 |
| 6,236,738 B1 * | 5/2001 | Zhu et al. | ...................... | 382/107 |
| 6,251,074 B1 * | 6/2001 | Averkiou et al. | ............ | 600/447 |
| 7,024,024 B1 * | 4/2006 | Aiazian | ......................... | 382/128 |
| 7,041,061 B2 * | 5/2006 | Kramer et al. | ............... | 600/508 |
| 7,054,679 B2 * | 5/2006 | Hirsh | ............................ | 600/523 |
| 2004/0260169 A1 * | 12/2004 | Sternnickel | .................. | 600/409 |
| 2005/0125150 A1 * | 6/2005 | Wang et al. | .................... | 701/213 |
| 2006/0211942 A1 * | 9/2006 | Hoctor et al. | ................ | 600/438 |
| 2007/0053589 A1 * | 3/2007 | Gering | ......................... | 382/173 |
| 2007/0197905 A1 * | 8/2007 | Timinger et al. | ............ | 600/407 |
| 2008/0194979 A1 * | 8/2008 | Madry et al. | ................. | 600/523 |
| 2008/0221450 A1 * | 9/2008 | Kim et al. | .................... | 600/443 |

* cited by examiner

*Primary Examiner* — James Kish
*Assistant Examiner* — Michael N Fisher
(74) *Attorney, Agent, or Firm* — Donald B. Paschburg

(57) ABSTRACT

A method for monitoring left ventricular (LV) myocardial wall thickness. The method includes: obtaining real time images of a periodically spatially changing myocardium and segmenting the myocardium in such images; calculating wall thickness of the myocardium from each one of the obtained images; and performing a dynamic harmonic analysis of the calculated thickness to determine spatial changes in the thickness of the wall of the myocardium. The method applies the calculated wall thickness to a predictor to determine changes in the thickness of the wall of the myocardium. The method applies the calculated wall thickness to a predictor to determine the periodicity the myocardium.

14 Claims, 4 Drawing Sheets

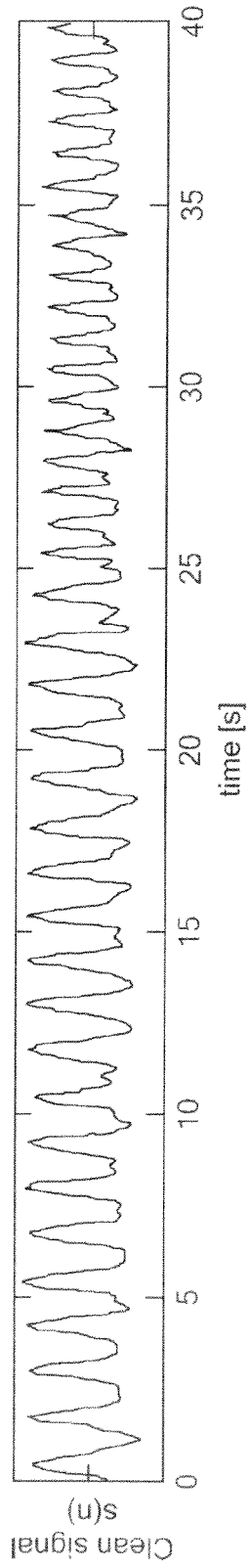
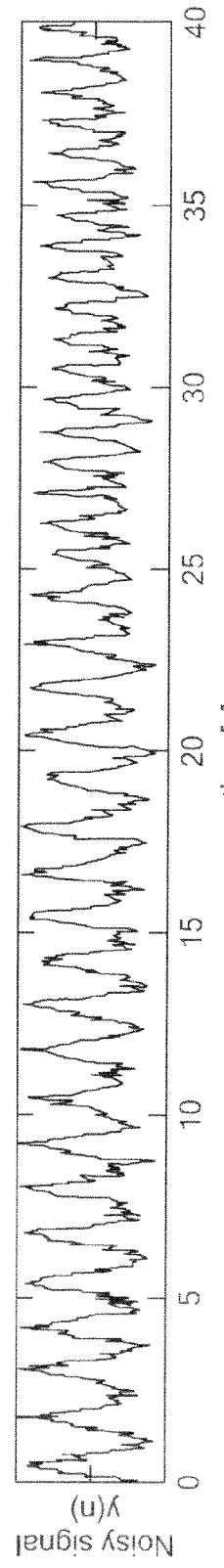

METHOD FOR MONITORING MYOCARDIAL WALL THICKNESS

CROSS-REFERENCE TO RELATED APPLICATIONS

This application claims priority from U.S. Provisional application No. 60/977,397 filed Oct. 4, 2007, the entire subject matter thereof being incorporated herein by reference.

TECHNICAL FIELD

This invention relates generally to methods for monitoring myocardial wall thickness and for detecting abrupt changes in such wall thickness.

BACKGROUND

As is known in the art, catheterization based methods like angioplasty, valve replacement, stent placement, and ablation for atrial fibrillation are widely performed under X-ray monitoring and guidance. This guidance method, however, involves the use of ionizing radiation the exposure of which to the patient and even more one for the medical personnel conducting the procedure should be minimized. MR would be a preferable alternative not just because of its non-ionizing technique but also because it provides superior soft tissue contrast in its images. One of the major issues still confronting interventional MR is that standard monitoring devices such as the ECG are disturbed by the magnetic field environment and cannot be interpreted during MR imaging. Real time updates on heart function and structure during a procedure are critical for interventional cardiovascular MRI in particular as well as interventional MRI in general.

As is also known in the art, it is frequently desirable to detect pathological changes in the left ventricular (LV) myocardial wall during a cardiovascular intervention or stress testing under MRI.

SUMMARY

In accordance with the present invention, a method is provided for monitoring a myocardium. The method includes: obtaining real time images of a periodically spatially changing myocardium and segmenting the myocardium in these images; calculating wall thickness of the myocardium from each one of the obtained images; and performing a dynamic harmonic analysis of the calculated thickness to determine spatial changes in the thickness of the wall of the myocardium.

In one embodiment, a method is provided for monitoring a myocardium. The method includes: obtaining real time images of myocardium and segmenting the myocardium in the obtained images; calculating wall thickness of the myocardium from each one of the obtained images; and applying the calculated wall thickness to a predictor to determine changes in the thickness of the wall of the myocardium.

In one embodiment, a method is provided for monitoring a myocardium. The method includes: obtaining real time images of a periodically spatially changing myocardium and segmenting the myocardium; calculating wall thickness of the myocardium from each one of the obtained images; and applying the calculated wall thickness to a predictor to determine the periodicity of the myocardium.

In one embodiment, a method is provided for monitoring myocardium. The method includes: obtaining real time images of a periodically spatially changing myocardium and segmenting the myocardium; calculating wall thickness of the myocardium from each one of the obtained images; applying the calculated wall thickness to a first predictor to determine the periodicity the myocardium; and applying the calculated wall thickness and the periodicity determined from the first predictor to a second predictor to determine changes in the thickness of the wall of the myocardium.

In one embodiment, the predictors are Kalman filters.

In one embodiment, a method is provided for monitoring left ventricular (LV) myocardial wall thickness. The method includes: obtaining real time images of a periodically spatially changing LV and segmenting the LV; estimating in real time wall thickness of the LV from the obtained images using a dynamic harmonic model of the LV comprising executing a recursive routine to determine an estimate of wall thickening level based upon the estimate.

In one embodiment, the method includes performing statistical testing of the LV statistical testing to determine abrupt changes in the wall thickness.

In one embodiment, the method includes determining the periodicity in the wall thickness.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A shows a time history of a simulated (clean) wall thickness signal, $S_t$ for a LV of a periodically varying (i.e., a beating heart), it being noted that at time 25 a simulation is made of injection of a pharmaceutical that would simulate an ischemic heart being placed in a stress condition.

FIG. 2B shows the time history of noise (the noise distribution was estimated based on real volunteer data) and is added to the clean signal in FIG. 2A.

Like reference symbols in the various drawings indicate like elements.

DETAILED DESCRIPTION

Figure 1:
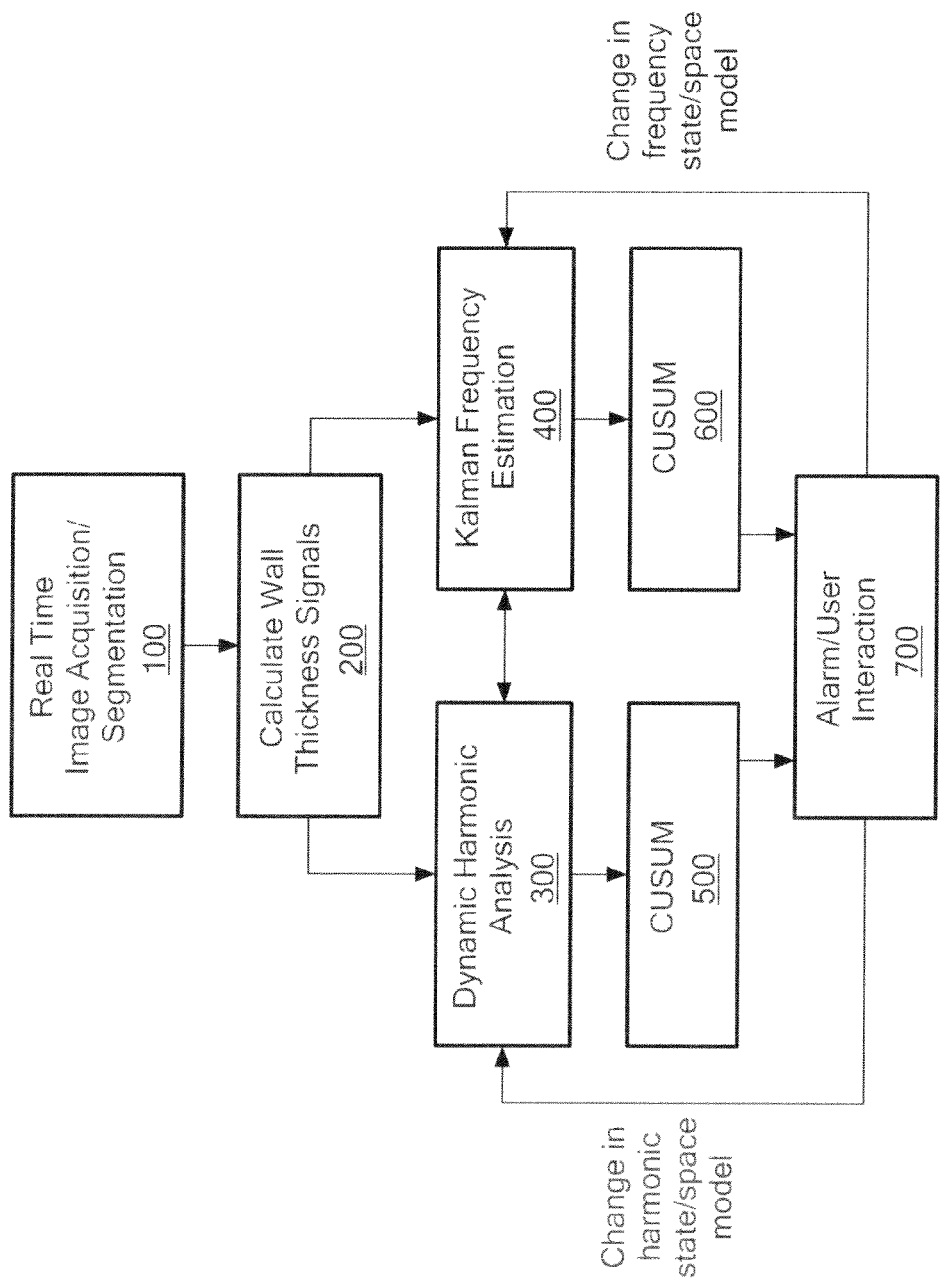
FIG. 1 is a flowchart of a method for monitoring myocardial wall thickness and detecting abrupt changes in such wall thickness according to the invention.

Referring now to FIG. 1, a flowchart is shown for a methodic for monitoring myocardial wall thickness and for detecting abrupt changes in such wall thickness is shown. As will be described in more detail below, the invention provides dynamic harmonic analysis and frequency tracking with CUSUM testing.

The method segments in real time images of the LV, Step 100. Here, the real time images are acquired on an MR Scanner and an existing and establish left ventricular (LV) segmentation such as described in a paper by Jolly, M. (2001), Combining Edge, Region, and Shape Information to Segment the Left Ventricle in Cardiac MR Images., in 'MICCAI', pp. 482-490 has been adapted to estimate the endocardial (inner) and epicardial (outer) contour of the LV myocardium, Step 200.

The contours are initialized with approximate localization of the left ventricle and a local deformation in the temporal domain as a starting point. Then they are propagated to adjacent temporal frames where the local deformation is applied. The original propagation method relies that phases for an entire cardiac cycle are available. In a real time image scenario we do not have any phase information about the current image therefore we changed the algorithm that way that the propagation copy the contours from the processor image to the next before the local deformation is applied.

The myocardial wall thickness is calculated for a region determined by the user according to the AHA 17 compound model such described in Cerqueira, M. D.; Weissman, N. J.; Dilsizian, V.; Jacobs, A. K.; Kaul, S.; Laskey, W. K.; Pennell, D. J.; Rumberger, J. A.; Ryan, T.; Verani, M. S.; on Myocardial Segmentation, A. H. A. W. G. & for Cardiac Imaging, R. (2002), 'Standardized myocardial segmentation and nomenclature for tomographic imaging of the heart: a statement for healthcare professionals from the Cardiac Imaging Committee of the Council on Clinical Cardiology of the American Heart Association.', Circulation 105(4), 539-542.

The measured values for each region result in a wall thickness signal $S_t$. Wall thickness measurements derived from MR images are subjects to a considerable measurement error. The thickness curves due not adequately reflect the smooth myocardial wall. This is due to errors in the automatically tracing of the endocardial and epicardial contours. The aim of this invention provides a mean to predict and estimate wall thickness in time and detect changes that might result in an alarm.

The wall thickness signal is a periodical signal. One period has the length of one heart beat. The harmonic decomposition of the signal shows that two harmonics are enough to model the signal adequately.

Therefore we could describe the wall thickness signal $S_t$ using the following state space model:

$$S_t = c_0 + \sum_{j=1}^{2} \left( c_j \cos(j\omega t + \sigma_{j,\lambda_j}) \right)$$

where:
$c_0$ is a constant;
$c_j$ are constants;
$\omega = 2\pi f$, where f is the beating frequency of the heart; and
$\sigma$ is phase
State Equation:

$$X_{t+1} = X_t + W$$

Where W is the process noise with distribution $W \sim N(0,Q)$ and X is the (5×1) state vector with $X=(c_0, a_1, b_1, a_2, b_2)$ With $$a_1 = c_1 \cdot \cos(\sigma_1)$$
$$b_1 = c_1 \cdot \sin(\sigma_1)$$
$$a_2 = c_2 \cdot \cos(\sigma_2)$$
$$b_2 = c_2 \cdot \sin(\sigma_2)$$

Observation Equation:

$$Y_t = HX_t + V$$

Y is the observation vector $(y_t, y_{t-1}, \ldots y_{t-m})$
V is the measurement noise with distribution $V \sim N(0,R)$
H (mx5) is the state/observation transformation matrix:

$$h_{0,k} = 1$$
$$h_{1,k}(k \cdot \Delta t) = \cos(2\pi f \Delta t)$$
$$h_{2,k}(k \cdot \Delta t) = -\sin(2\pi f \Delta t)$$
$$h_{3,k}(k \cdot \Delta t) = \cos(4\pi f \Delta t)$$
$$h_{4,k}(k \cdot \Delta t) = -\sin(4\pi f \Delta t)$$

k=1 . . . m is the number of samples and $\Delta t$ is the sampling interval.

The wall thickness measurements are fed to a pair of regressive filters (i.e., predictors), here Kalman filters 300, 400; one (300) for removing noise on the wall thickness measurement signal and the other (400) for measuring the frequency, f, of the beating heart.

For this state space model the Kalman filter is applied. This could be treated with the Kalman algorithm. The Kalman filter is suited to solve this prediction problem since it does not need deterministic dynamics or stationary properties.

In the above section we assumed that the frequency is constant which is not the case in a real life scenario. Therefore we introduce a second Kalman filter to track the frequency, which is measured either by means of the ECG or using short time FFT in the wall thickness signal. The Frequency tracker has the following simple
State Space Model Wall Thickness Frequency:
State and Observation Equations:

$$F_{t+1} = F_t W_F$$
$$Z_F = F_t + V_F$$

where the state vector F consists in the frequency f, $W_F \sim N(0, Q_F)$ is the process noise and $V_F \sim N(0, R_F)$ the measurement noise.

Initialization:

The state vector will be initialized with values determined by a FFT which is obtained at an initialization phase at the beginning of the monitoring process. The measurement and process noise will be determined by the user with an initial guess or estimate. Better possibilities of estimating these noise distribution are still under investigation.

EXAMPLE

Figure 2C:
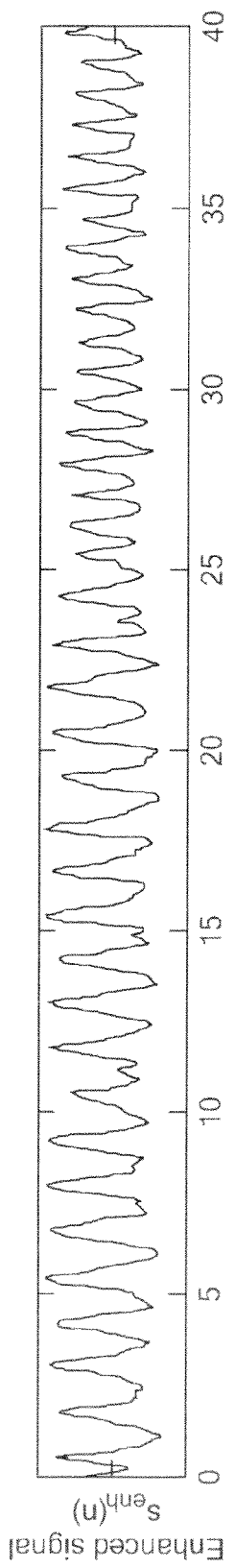
FIG. 2C shows the output of a predictor in response to the signal of FIG. 2B applied to the predictor.
Figure 2D:
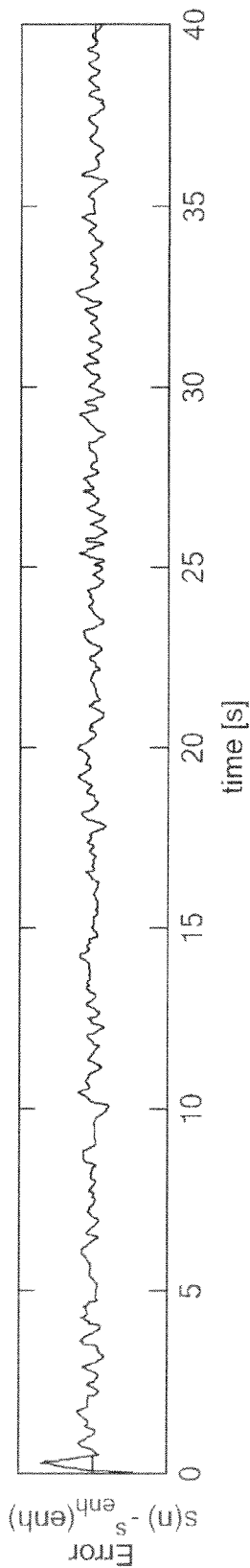
FIG. 2D shows an error signal between the signal shown in FIG. 2C and the signal shown in FIG. 2B.

FIG. 2A shows a simulated (clean) wall thickness signal for a LV of a periodically varying (i.e., a beating heart). It is noted that at time 25 a simulation is made of injection of a pharmaceutical that you would simulate the heart being placed in a stress condition. In FIG. 2B noise (the noise distribution was estimated based on real volunteer data) and is added to the clean signal in FIG. 2A. A predictor, here a regressive filter, here a Kalman filter is applied to the signal FIG. 2B to produce the signal shown in FIG. 2C. The error between the signal shown in FIG. 2C and the signal shown in FIG. 2B is shown in FIG. 2D.

Figure 2E:
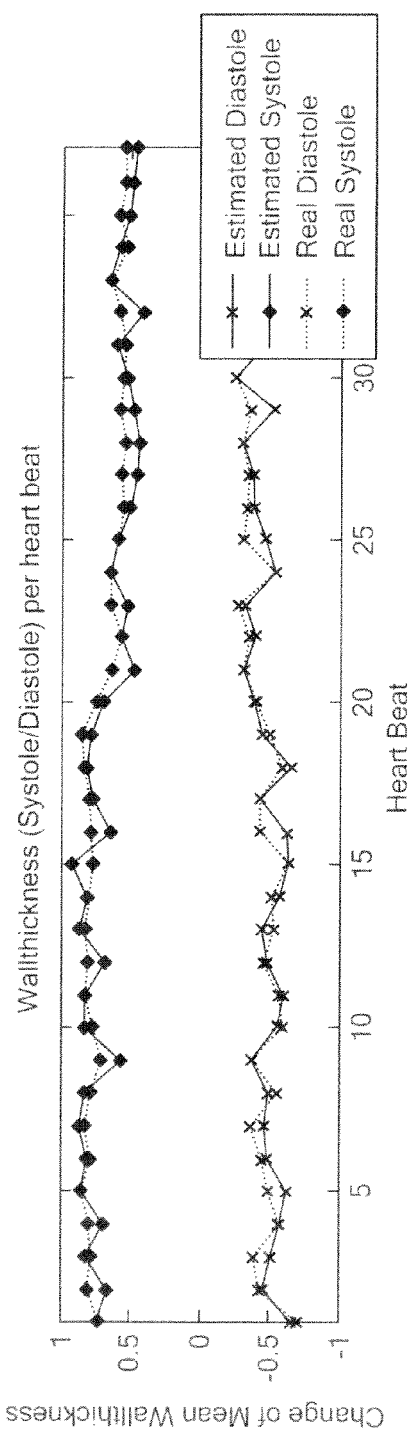
FIG. 2E shows an upper pair of signals being an estimated mean wall thinness of an LV when a heart is in a systolic condition as determined from the predictor and the actual wall thickness of the LV when the heart is in a systolic condition and the lower pair of signals being the estimated mean wall thinness of the LV when the heart is in a diastolic condition as determined from the Kalman filter (predictor) and the actual wall thickness of the LV when the heart is in the diastolic condition.

Referring to FIG. 2E, the upper pair of signals is the estimated mean wall thinness of the LV when the heart is in a systolic condition as determined from the Kalman filter (predictor) and the actual wall thickness of the LV when the heart is in a systolic condition. The lower pair of signals is the estimated mean wall thinness of the LV when the heart is in a diastolic condition as determined from the Kalman filter (predictor) and the actual wall thickness of the LV when the heart is in the diastolic condition.

The quotient of the estimated one of the upper pair of signals to the estimated lower one of the pair of signals is used by clinician to evaluate the viability of the myocardium.

Figure 2F:
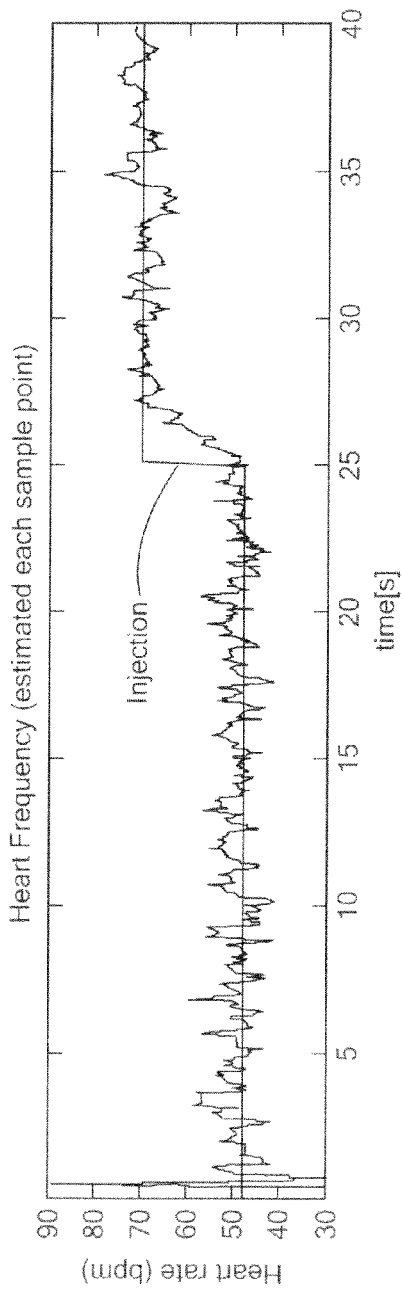
FIG. 2F shows the signal by a predictor for estimating the frequency of the periodically changing LV as a result of the beating heart, it being noted that the heart beat increases in frequency (i.e., periodicity) at time 25.

FIG. 2F shows the signal by a predictor for estimating the frequency of the periodically changing LV as a result of the beating heart, it being noted that the heart beat increases in frequency (i.e., periodicity) at time 25.

Two CUSUM (statistical processing) algorithms 500, 600 are applied to detect rapid changes in the estimated measurements errors:

(a) the wall thickness itself, here the difference between the predicted (the result of the state equation) and the estimated (included the measurement) is tested (b) the mean and variance of the frequency estimation and prediction is tested a change occurs in both cases if a significant difference between the estimated and the prediction occurs or a significant difference between consecutive residuals are found.

Alarm/Feedback:

If the CUSUM test is positive an alarm is given and/or a feedback is given to the estimation algorithm to reset the Kalman filters and take the current state vectors as initial values, Step 700.

A number of embodiments of the invention have been described. Nevertheless, it will be understood that various modifications may be made without departing from the spirit and scope of the invention. Accordingly, other embodiments are within the scope of the following claims.

What is claimed is:

1. A computer-implemented method for real time monitoring of a myocardium during a cardiovascular procedure, the method implemented by the computer comprising the steps of:

acquiring real time images of a left ventricle (LV) myocardium for a plurality of time steps and segmenting in real time the myocardium in each said image to estimate the endocardial and epicardial contours of the LV myocardium;

calculating a wall thickness of the myocardium in real-time from the estimated endocardial and epicardial contours for each said segmented image;

using a first state space model with a first regressive filter to predict the myocardium wall thickness for each acquired real time image over the plurality of time steps based on the previously acquired real time images and an estimated cardiac beating frequency, wherein the first state space model of the myocardium wall thickness is $$S_t = c_0 + \sum_{j=1,2} (c_j \cos(jwt + \sigma_j)),$$

wherein $c_0$ and $c_1$ are constants $w=2\pi f$ wherein f is the estimated cardiac beating frequency, and $\sigma_j$ is a phase; and using the predicted myocardium wall thickness with a second state space model with a second regressive filter to predict a cardiac beating frequency for each acquired real time image over the plurality of time steps based on the previously acquired real time images, wherein at each subsequent time step the estimated cardiac beating frequency is updated with the predicted cardiac beating frequency in the first state space model.

2. The method of claim 1, further comprising initializing endocardial and epicardial contours for a first real time image from the estimated endocardial and epicardial contours, propagating said initialized endocardial and epicardial contours to a subsequently acquired real time image and applying a local deformation to said contours.

3. The method of claim 1, wherein the first regressive filter estimates at each time step a coefficient vector ($c_0$, $a_1$, $b_1$, $a_2$, $b_2$) based on the first state space model from the myocardium wall thicknesses calculated for each segmented image, wherein $$a_1 = c_1 \cos(\sigma_1), b_1 = c_1 \sin(\sigma_1), a_2 = c_2 \cos(\sigma_2), \text{ and } b_2 = c_2 \sin(\sigma_2).$$

4. The method of claim 1, further comprising applying a CUSUM algorithm to a difference between the predicted myocardium wall thickness and the calculated myocardium wall thickness to detect a rapid change in the differences.

5. The method of claim 1, further comprising applying a CUSUM algorithm to a mean and variance of the predicted cardiac beating frequency and the estimated cardiac beating frequency to detect changes between the predicted cardiac beating frequency and the estimated cardiac beating frequency, and to detect significant changes between predicted cardiac beating frequencies for consecutive time steps and between estimated cardiac beating frequencies for consecutive time steps.

6. The method of claim 5, wherein the estimated cardiac beating frequency is determined using a fast Fourier transform of the calculated myocardium wall thickness.

7. A computer-implemented method for real time monitoring of a myocardium during a cardiovascular procedure, the method implemented by the computer comprising the steps of:

acquiring real time images of a left ventricle (LV) myocardium for a plurality of time steps and segmenting in real time the myocardium in each said image to estimate the endocardial and epicardial contours of the LV myocardium;

calculating a wall thickness of the myocardium in real time from the estimated endocardial and epicardial contours for each said segmented image;

using a first state space model with a first regressive filter to predict the myocardium wall thickness for each acquired real time image over the plurality of time steps based on the previously acquired real time images and an estimated cardiac beating frequency, wherein the first state space model of the myocardium wall thickness is $$S_t = c_0 + \sum_{j=1,2} (c_j \cos(jwt + \sigma_j)),$$

wherein $c_0$ and $c_j$ are constants, $w=2\pi f$ wherein f is the estimated cardiac beating frequency, and $\sigma_j$ is a phase, and the first regressive filter estimates at each time step a coefficient vector ($c_0$, $a_1$, $b_1$, $a_2$, $b_2$) based on the first state space model from the myocardium wall thicknesses calculated for each segmented image, wherein $$a_1 = c_1 \cos(\sigma_1), b_1 = c_1 \sin(\sigma_1), a_2 = c_2 \cos(\sigma_2), \text{ and } b_2 = c_2 \sin(\sigma_2).$$

8. The method of claim 7, further comprising using the predicted myocardium wall thickness with a second state space model with a second regressive filter to predict a cardiac beating frequency for each acquired real time image over the plurality of time steps based on the previously acquired real time images, wherein at each subsequent time step the estimated cardiac beating frequency is updated with the predicted cardiac beating frequency first state space model.

9. A non-transitory program storage device readable by a computer, tangibly embodying a program of instructions executable by the computer to perform the method steps for real time monitoring of a myocardium during a cardiovascular procedure, the method comprising the steps of:

acquiring real time images of a left ventricle (LV) myocardium for a plurality of time steps and segmenting in real time the myocardium in each said image to estimate the endocardial and epicardial contours of the LV myocardium;

calculating a wall thickness of the myocardium in real-time from the estimated endocardial and epicardial contours for each said segmented image;

using a first state space model with a first regressive filter to predict the myocardium wall thickness for each acquired real time image over the plurality of time steps based on the previously acquired real time images and an estimated cardiac beating frequency, wherein the first state space model of the myocardium wall thickness is $$S_t = c_0 + \sum_{j=1,2} (c_j \cos(jwt + \sigma_j)),$$

wherein $c_0$ and $c_j$ are constants, $w=2\pi f$ wherein f is the estimated cardiac beating frequency, and $\pi_j$ is a phase; and using the predicted myocardium wall thickness with a second state space model with a second regressive filter to predict a cardiac beating frequency for each acquired real time image over the plurality of time steps based on the previously acquired real time images, wherein at each subsequent time step the estimated cardiac beating frequency is updated with the predicted cardiac beating frequency first state space model.

10. The computer readable program storage device of claim 9, the method further comprising initializing endocardial and epicardial contours for a first real time image from the estimated endocardial and epicardial contours, propagating said initialized endocardial and epicardial contours to a subsequently acquired real time image and applying a local deformation to said contours.

11. The computer readable program storage device of claim 9, wherein the first regressive filter estimates at each time step a coefficient vector $(c_0, a_1, b_1, a_2, b_2)$ based on the first state space model from the myocardium wall thicknesses calculated for each segmented image, wherein $$a_1 = c_1 \cos(\sigma_1), b_1 = c_1 \sin(a_2 = c_2 \cos(\sigma_2), \text{and } b_2 = c_2 \sin(\sigma_2).$$

12. The computer readable program storage device of claim 9, the method further comprising applying a CUSUM algorithm to a difference between the predicted myocardium wall thickness and the calculated myocardium wall thickness to detect a rapid change in the differences.

13. The computer readable program storage device of claim 9, the method further comprising applying a CUSUM algorithm to a mean and variance of the predicted cardiac beating frequency and the estimated cardiac beating frequency to detect changes between the predicted cardiac beating frequency and the estimated cardiac beating frequency, and to detect significant changes between predicted cardiac beating frequencies for consecutive time steps and between estimated cardiac beating frequencies for consecutive time steps.

14. The computer readable program storage device of claim 13, wherein the estimated cardiac beating frequency is determined using a fast Fourier transform of the calculated myocardium wall thickness.

* * * * *